United States Patent
Klyosov et al.

(10) Patent No.: US 7,012,068 B2
(45) Date of Patent: *Mar. 14, 2006

(54) CO-ADMINISTRATION OF A POLYSACCHARIDE WITH A CHEMOTHERAPEUTIC AGENT FOR THE TREATMENT OF CANCER

(75) Inventors: Anatole Klyosov, Newton, MA (US); David Platt, Newton, MA (US)

(73) Assignee: Pro-Pharmaceuticals, Inc., Newton, MA (US)

(*) Notice: Subject to any disclaimer, the term of this patent is extended or adjusted under 35 U.S.C. 154(b) by 635 days.

This patent is subject to a terminal disclaimer.

(21) Appl. No.: 10/108,237

(22) Filed: Mar. 27, 2002

(65) Prior Publication Data

US 2003/0064957 A1 Apr. 3, 2003

Related U.S. Application Data

(63) Continuation-in-part of application No. 09/818,596, filed on Mar. 27, 2001, now Pat. No. 6,645,946.
(60) Provisional application No. 60/317,092, filed on Sep. 4, 2001.

(51) Int. Cl.
*A01N 43/04* (2006.01)
*A61K 31/715* (2006.01)
*A61K 31/70* (2006.01)
*A61K 31/505* (2006.01)

(52) U.S. Cl. .............................. 514/54; 514/23; 514/34; 514/256; 514/974

(58) Field of Classification Search ................ 514/23, 514/34, 54, 256, 974
See application file for complete search history.

(56) References Cited

U.S. PATENT DOCUMENTS

| 5,118,673 | A | * | 6/1992 | Carpenter et al. | ............. 514/54 |
|---|---|---|---|---|---|
| 5,773,425 | A | | 6/1998 | McAnalley et al. | ........... 514/54 |
| 5,786,342 | A | | 7/1998 | Carpenter et al. | ............. 514/54 |
| 5,834,442 | A | * | 11/1998 | Raz et al. | ..................... 514/54 |
| 5,861,142 | A | * | 1/1999 | Schick | ........................ 424/61 |
| 2001/0026807 | A1 | | 10/2001 | Watts | |
| 2001/0036473 | A1 | | 11/2001 | Scott et al. | |
| 2002/0044967 | A1 | | 4/2002 | Yamashita et al. | |
| 2002/0058061 | A1 | | 5/2002 | Midha et al. | |

FOREIGN PATENT DOCUMENTS

| EP | 0721784 | 7/1996 |
|---|---|---|
| JP | 06256196 | 9/1994 |

OTHER PUBLICATIONS

"Synthesis and Cytotoxic Activity of Oxidized Galactomannan/ADR Conjugate", J.M.S. Pure Applied Chemistry, 1997, A34(6), pp. 975–989.*

* cited by examiner

*Primary Examiner*—James O. Wilson
*Assistant Examiner*—Traviss C. McIntosh, III
(74) *Attorney, Agent, or Firm*—Stephen J. Gaudet; Perkins, Smith & Cohen, LLP

(57) ABSTRACT

Methods and compositions for treating cancer with a formulation are provided in which a polysaccharide, galactomannan, is co-administered with a therapeutic agent to a subject to reduce toxicity and/or enhance efficacy of the agent for the subject.

25 Claims, No Drawings

CO-ADMINISTRATION OF A POLYSACCHARIDE WITH A CHEMOTHERAPEUTIC AGENT FOR THE TREATMENT OF CANCER

CROSS REFERENCE TO RELATED APPLICATIONS

This application claims priority from, and is a continuation-in-part application of, U.S. patent application Ser. No. 09/818,596, filed Mar. 27, 2001, now U.S. Pat. No. 6,645,946, and also claims priority from U.S. Provisional Application No. 60/317,092 filed Sep. 4, 2001, both of which are herein incorporated by reference.

TECHNICAL FIELD AND BACKGROUND ART

The present invention relates to administration of a toxic agent to a subject with cancer, in a formulation in which toxicity is substantially reduced and/or therapeutic efficacy enhanced. The most widely used methods to treat cancer are surgery, radiation and chemotherapy. Cancer patients often receive a combination of these treatments and about half of all patients receive chemotherapy. Unfortunately, chemotherapeutic agents have significant limitations relating to their toxic effect on the patient and the efficacy of a particular dosage to target and kill tumor cells.

BACKGROUND

Most chemotherapy agents kill cancer cells by disrupting the cell division process. Cells are killed once they begin to undergo division and replication. Although these agents are effective for treating cancer cells which generally grow rapidly through unregulated cell division, they also kill healthy non-cancerous cells as they undergo ordinary cell division. This toxic effect is particularly apparent in fast-growing normal cells, such as bone marrow cells, those in the digestive tract, hair follicles, and reproductive cells. Because chemotherapy harms healthy tissue, the effectiveness of the drug is limited by dosage levels and treatment frequency which should not exceed tolerance levels for non-cancerous cells. Moreover, the chemotherapy regimen often dramatically diminishes the quality of a patient's life through its physical and emotional side effects. Without the ability to target the drug exclusively to cancerous tissue, chemotherapy dosages must be kept within a range that healthy tissue can tolerate, thus reducing the optimal effectiveness of chemotherapy on diseased tissue. If the toxicity of chemotherapeutic agents could be reduced, the clinician would be able to increase the dosage of drug without causing unacceptable side effects. Increasing efficacy of a drug can be translated into decreasing of the dosage of the drug, which again minimizes the harmful effects on the patient while offering maximum benefit. Decreasing dosage by increasing efficacy of a chemotherapeutic drug together with a reduction in toxic effects would lead to improvement of the patient's quality of life through controlling the tumor and through harmful side effects.

SUMMARY OF THE INVENTION

In a first embodiment of the invention there is provided a method for treating a cancer in a subject, that includes obtaining a mixture of galactomannan polysaccharide and an effective dose of a chemotherapeutic agent in a pharmaceutically acceptable formulation; and administering the formulation to the subject so as to treat the cancer.

In additional embodiments, the mixture contains an amount of galactomannan and the therapeutic agent in a ratio suitable for reducing a toxic effect in the subject, the toxic effect resulting from administration of a cancer-reducing amount of the chemotherapeutic agent absent galactomannan, the mixture optionally enhancing efficacy of chemotherapeutic effect for treating the cancer.

In further embodiments of the method, the molecular weight of the galactomannan is in the range of 20,000–600,000 D, for example the galactomannan has a molecular weight in the range of 90,000 to 415,000 D or 40,000–200,000 D, for example, the galactomannan has an average molecular weight of 83,000 D or 215,000 D. The galactomannan may be a derivative of an isolate from *Gleditsia triacanthos* or from *Medicago falcate* or from *Cyamopsis tetragonoloba*.

In further embodiments, the galactomannan may be β-1→4-D-galactomannan and include a ratio of galactose to mannose where mannose is in the range of 1.0–3.0 and galactose is in the range of 0.5–1.5. Alternatively, the galactomannan includes a ratio of 2.6 mannose to 1.5 galactose.

In further embodiments, the galactomannan includes a ratio of 2.2 mannose to 0.9 galactose. Alternatively, the galactomannan may include a ratio of 1.13 mannose to 1 galactose. Alternatively, the galactomannan includes a ratio of 2.2 mannose to 1 galactose.

In further embodiments, the galactomannan and the chemotherapeutic agent are present in the mixture in a ratio of 0.1:1 w/w to 10:1 w/w.

In further embodiments, the mixture has a reduced toxicity of greater than 50% compared with the same dose of the agent absent galactomannan. For example, the mixture has a reduced toxicity of greater than 80% compared with the same dose of the agent absent galactomannan.

In embodiments of the invention, the chemotherapeutic agent is 5-FU. The cancer may be any of chronic leukemia, breast cancer, sarcoma, ovarian carcinoma, rectal cancer, throat cancer, melanoma, colon cancer, bladder cancer, lung cancer, mammary adenocarcinoma, gastrointestinal cancer, stomach cancer, prostate cancer, pancreatic cancer, or Kaposi's sarcoma. For example, the cancer may be any of breast cancer, colon cancer, or pancreatic cancer. Any of the above is applicable to a human subject.

In an embodiment of the invention, a pharmaceutical formulation is provided that includes a mixture of galactomannan polysaccharide and an effective dose for treating cancer of a chemotherapeutic agent in a pharmaceutically acceptable formulation. The mixture in the formulation may contain an amount of galactomannan and the therapeutic agent in a ratio suitable for reducing a toxic effect in the subject, the toxic effect resulting from administration of a cancer treating amount of chemotherapeutic agent absent galactomannan. Furthermore, the mixture may contain an amount of galactomannan and the therapeutic agent in a ratio suitable for enhancing efficacy of chemotherapeutic effect for treating the cancer.

In an embodiment of the invention, a method is provided where the mixture contains an amount of galactomannan and the therapeutic agent in a ratio suitable for enhancing efficacy of chemotherapeutic effect for treating the cancer. For any of the above, the formulation may be in a powder form or in a liquid form.

In an embodiment of the invention, a method is provided for obtaining a mixture of galactomannan polysaccharide and an effective dose of a chemotherapeutic agent formulated so that the chemotherapeutic agent has reduced toxicity in the presence of the galactomannan, the formulation being suitable for parenteral administration to the subject; and administering the formulation to the subject so as to treat the cancer.

In an embodiment of the invention, a method is provided for treating cancer in a subject, that includes obtaining an effective dose of a mixture of galactomannan polysaccharide and an effective dose of a chemotherapeutic agent formulated so that the chemotherapeutic agent has enhanced therapeutic efficacy in the presence of the galactomannan, the formulation being suitable for parenteral administration to the subject; and administering the formulation to the subject so as to treat the cancer. A method according to the above claims wherein the chemotherapeutic agent is adriamycin or 5 fluorouracil. A method according to any of the above embodiments wherein the enhanced therapeutic effect is a synergistic effect.

DETAILED DESCRIPTION OF EMBODIMENTS

As used in this description and the accompanying claims, the following terms shall have the meanings indicated, unless the context otherwise requires.

"Subject" refers to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

"Patient" refers to a human subject who has presented at a clinical setting with a particular symptom or symptoms suggesting the need for treatment.

"Polysaccharide" refers to polymers comprised primarily of monomers of one or more sugars and substituted sugars. When isolated from nature, polysaccharide preparations comprise molecules that are commonly heterogeneous in molecular weight.

"Efficacy" for a toxic therapeutic agent refers to the relationship between a minimum effective dose and an extent of toxic side effects. Efficacy of an agent is increased if a therapeutic end point can be achieved by administration of a lower dose or a shorter dosage regimen. If toxicity can be decreased, a therapeutic agent can be administered on a longer dosage regimen or even chronically with greater patient compliance and improved quality of life. Further, decreased toxicity of an agent enables the practitioner to increase the dosage to achieve the therapeutic endpoint sooner, or to achieve a higher therapeutic endpoint. "Efficacy" for a non-toxic therapeutic agent relates to improved therapeutic effect for treating a condition.

"Pharmaceutically acceptable carrier" refers to any and all solvents, dispersion media, e.g., human albumin or cross-linked gelatin polypeptides, coatings, antibacterial and antifungal agents, isotonic, e.g., sodium chloride or sodium glutamate, and absorption delaying agents, and the like that are physiologically compatible. The use of such media and agents for pharmaceutically active substances is well known in the art. Preferably, the carrier is suitable for oral, intravenous, intramuscular, subcutaneous, parenteral, spinal or epidural administration (e.g., by injection or infusion). Depending on the route of administration, the active compound can be coated in a material to protect the compound from the action of acids and other natural conditions that can inactivate the compound.

"Parenteral administration" includes administration by bolus injection or infusion, as well as administration by intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

"Toxic" refers to any adverse effect caused by an agent when administered to a subject.

"Tumor regression" was scored (excluding nonspecific deaths) as "partial" (less than 50 percent of its size at the beginning of treatment), or "complete" (tumor becomes unpalpable).

"Duration of regression" refers to the interval during which a tumor classified as a partial or complete regression continues to be below 50 percent of its size at first treatment.

"Evaluation size" refers to the tumor mass selected at one or two mass doubling beginning with the initial tumor size at the start of treatment.

"Time required for tumor mass doubling" is the time to reach the evaluation size; it is used in the calculations of the overall delay in the growth of the median tumor [(T−C)/C× 100%], where T−C (days) is the difference in the median of times postimplant for tumors of the treated (T) groups to attain an evaluation size compared to the median of the control (C) group. The T−C value is measured excluding nonspecific deaths, and any other animal that dies whose tumor failed to attain the evaluation size.

We provide a method for treating a subject with a therapeutic agent that minimizes the toxic side effects of the therapeutic agent and may additionally enhance its therapeutic efficacy. The method requires the co-administration of the agent with a polysaccharide.

Although the examples provided herein describe the beneficial effects of galactomannans, we do not exclude the possibility that other polysaccharides may have a similar effect. The observed reduction in toxicity of a toxic therapeutic agent makes it possible to administer a greater dose without an increase in adverse side effects associated with treatment. The administration of increased dosages of a therapeutic agent having toxic side effects may be beneficial for treatment of a number of diseases including cancer, where the toxic side effects of traditional cytotoxic agents have limited their use.

In addition to reducing toxicity, efficacy of the therapeutic effect may be enhanced by administering a therapeutic agent with a galactomannan. The increase in efficacy may arise from a synergistic effect between the galactomannan and the therapeutic agent mixture.

Both the polysaccharide and the agent may separately be formulated, in a dry form for example as a powder, or in a liquid form. In a preferred embodiment, the polysaccharide and therapeutic agent are mixed prior to administration. The mixture may be in the form of a liquid, a powder or an aerosol.

The dosage regimens for established chemotherapeutic agents with known toxic side effects has been established and are described in the Physician's Desk Reference. For example, a description of adriamycin can be found in the Physician's Desk Reference $48^{th}$ Edition (1994) pp. 459–461 and for 5-fluorouracil (5-FU) on pages 1924–1925, these descriptions being incorporated by reference. The co-administration of polysaccharide with a therapeutic agent may utilize but is not limited to the dosage regimen and route of administration already established and approved for the therapeutic agent, the difference being the inclusion of the polysaccharide. For example, a single bolus can be administered, several divided doses can be administered over a period of time, or a dose can be proportionally reduced and administered over a time period by infusion, or can be increased, as indicated by the exigencies of the therapeutic situation. The dosage unit will be a mixture of polysaccharide with therapeutic agent. However, we do not exclude the possibility that the polysaccharide and therapeutic agent could be administered sequentially as distinct formulations.

The formulation of the mixture may be derived from the standard formulation of the therapeutic agent to which the polysaccharide is added in a compatible solvent or as a powder. For example, the chemotherapeutic agent 5-FU is commonly formulated in an aqueous solution with excipients. In Example 1, aqueous galactomannan was added to the aqueous 5-FU to provide the formulation that was administered to the subject.

Pharmaceutically acceptable carriers are commonly added in typical drug formulations. For example in oral formulations, hydroxypropyl cellulose, colloidal silicon dioxide, magnesium carbonate, methacrylic acid copolymer, starch, talc, sugar sphere, sucrose, polyethylene glycol, polysorbate 80, and titanium dioxide: croscarmellose sodium, edible inks, gelatin, lactose monohydrate, magnesium stearate, povidone, sodium lauryl sulfate, camuba wax, crospovidone, hydroxypropyl methylcellulose, lactose, microcrystalline cellulose, and other ingredients may be used. In addition, galactomannan has been used as a carrier for oral delivery of agents, which are in a non-liquid form. (U.S. Pat. Nos.: 4,447,337; 5,128,143; and 6,063,402).

One of ordinary skill in the art can determine and prescribe the effective amount of the therapeutic composition required based on clinical protocols. In general, a suitable daily dose of a composition of the invention will be that amount of the composition, which is the lowest dose effective to produce a therapeutic effect.

Embodiments of the invention demonstrate that administration of a mixture of a polysaccharide and a cytotoxic therapeutic may result in reduced toxicity and may further provide an enhanced therapeutic effect in comparison with the therapeutic agent in the absence of the polysaccharide. A mixture may be formed from galactomannan and any synthetic therapeutic agent so as to achieve enhanced efficacy of therapeutic effect of the agent. An example of a polysaccharide with this activity is galactomannan. Galactomannan may be obtained from a variety of natural sources such as plants and may be made synthetically by enzymatic reactions or by chemical synthesis. Examples 1 and 2 show the effects of using galactomannans derived from two separate plant sources which have been demonstrated to be effective at reducing toxicity of therapeutic agents. In particular, Example 1 describes the use of galactomannan from a second plant species *Gleditsia triacanthos* and Example 2 describes the use of galactomannan obtained from the plant species *Medicago falcata*.

Galactomannan is a polymer that may occur in a variety of size ranges. Moreover, the galactomannan may be derivatized or hydrolyzed to result in fragments of the native molecule or may be reacted to provide chemically modified forms of the native molecule. Embodiments of the invention provide a galactomannan having a molecular weight in the range of 20,000–600,000 D. The galactomannan may further have a size in the range of 90–415,000 D or 40,000–200,000 D. Example 1 utilizes a galactomannan with an average molecular weight of 215,000 D while Example 2 utilizes a galactomannan with an average molecular weight of 83,000 D.

The ratio of mannose to galactose may vary according to the source of the galactomannan and the isolation procedure. In embodiments of the invention, the galactomannan may have a mannose to galactose ratio of 1–3 mannose: 0.3–1.5 galactose. The ratio of mannose to galactose may be 2.6:1.5 or 2.2:0.9 or 1.13:1 or 2.2:1. In Example 1, the ratio of mannose to galactose is 2.2:1 and in Example 2, the selected ratio of mannose to galactose in the galactomannan is 1.13:1. In Example 3, the galactomannan has a mannose to galactose ratio of 2.2:1.0.

The galactomannan may be provided with the therapeutic agent in a mixture at a ratio of 0.1:1 w/w to 10:1 w/w with the therapeutic agent. In Example 1, the ratio of galactomannan to 5-FU is 1:1.9 and in Example 2 the ratio of galactomannan to adriamycin is 1:0.6. In Example 3, the ratio of galactomannan to 5-FU is 1.6:1. The results shown in Examples 1 and 2 are show significant reduction in toxicity when chemotherapeutic agents are administered in the presence of galactomannan. In Example 3, the results show significant increase in efficacy observed when chemotherapeutic agents are administered in the presence of galactomannan.

These results are dramatic as shown in Example 1 where instead of a death rate of 3/5 mice with 5-FU with the surviving mice showing substantial lack of normal weight increase, the same dose administered with galactomannan results in 0/5 mice dying. All mice survive and the surviving mice have weights equivalent to control mice (treated with saline). The surviving mice appear normal in all aspects with no sign of toxicity. In Example 2, the results demonstrate the advantages of formulating a mixture of adriamycin with galactomannan. Animals treated with an $LD_{50}$ dose of adriamycin according to standard toxicity tests result in a mortality of 3/5 mice. In contrast, when adriamycin is coadministered with adriamycin, the toxicity is reduced so that only 1/5 mice die. Moreover although there is some weight loss in the mice that survive, this weight loss is diminished.

In Example 3, a substantial reduction in tumor weight was observed in which tumor mass in control untreated mice was 2,058 mg and in mice treated with 75 mg/kg of 5-FU, tumor mass was 2,254 mg at 56 days after the initiation of treatment (the last day of the study). The same dose of 5-FU administered with galactomannan resulted in a tumor weight of 405 mg. Thirty-five days after the initiation of treatment, tumor weight was 2,450 mg (control, untreated), 990 mg (5-FU, 75 mg/kg), and 288 mg (same dose of 5-FU in combination with galactomannan). Twenty-eight days after the initiation of treatment, tumor weight was 1,296 mg (control, untreated), 527 mg (5-FU, 75 mg/kg), and 144 mg (same dose of 5-FU in combination with galactomannan).

In a preferred embodiment, the structure of galactomannans is a poly-β-1→4-mannan backbone, with the side substituents bound via α-1→6-glycoside linkages, for example:

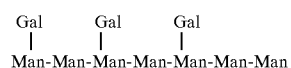

Without being bound by any particular theory, three possible mechanisms may account for the beneficial effect of galactomannan in a mixture with a cytotoxic or chemotherapeutic drug. One involves a direct physical interaction between the drug and galactomannan. For example, galactomannan may increase cancer cell membrane fluidity and permeability, as a result of galactose-specific interactions at the surface of the target cell. The polysaccharide can thus serve as an effective vehicle for delivery of the drug to the target. With respect to the treatment of cancer with chemotherapeutic agents, galactomannan may act to inhibit aggregation of tumor cells and their adhesion to normal cells, so that the cancer fails to metastasize. Once the polymer drug conjugate enters the tumor, which galactomannan recognizes by virtue of its structure and composition, galactomannan may release the anti-cancer drug. The toxicity of the chemotherapy drug may be reduced because the drug is inactive as long as it is bound to the polymer. Once the polymer drug conjugate enters the tumor, which galactomannan recognizes by virtue its structure and composition, galactomamman may release the anticancer drug. Another possible mode of action of galactomannan may involve its interaction with some regulatory sites in a biological system, particularly if those sites are governed by galactose-specific residues, such as galectins. Yet another possible mode of action may involve an inhibitory effect of galactomannans of a certain chemical structure (a certain Man:Gal ratio) and a certain size (molecular weight) on enzymatic systems responsible for a rapid clearance of 5-FU in the body, and therefore may potentially increase the bioavailability and prolong the mean residence time of 5-FU in the body, thus improving the therapeutic profile of 5-FU in cancer therapy.

Use of the galactomannan containing formulation can have an immediate effect of increasing the responses of patients to the chemotherapy, for example, an effect is a decrease in the dosage of the agent required for effective chemotherapy, in the presence of the formulation. It can have an immediate beneficial effect for the patient by decreasing toxicity of the drugs as here exemplified but not limited to adriamycin and 5 FU, and thereby improving a patient's quality of life.

The use of galactomannan administered in a mixture with a cytotoxic agent can be applied to a wide range of agents and is not restricted to anti-tumor or anti-cancer agents. Therapeutic areas include anti-depressants, anti-inflammatory agents, gastroenterology drugs (for treating ulcers and associated disorders), anti-psychotic drugs, anti-hyperlipidemic agents, etc. As many therapeutic agents must be administered as a chronic medicine, i.e., on a long-term basis, potential reduction in dosage and improvement in quality of life become significant factors in availability, cost of therapeutic agents, and patient compliance.

Examples of chemotherapeutic agents according to embodiments of the invention include: 1.alkylating agents such as mustargen-nitrogen mustard, cyclophosphamide (cytoxan), melphalan (alkeran), chlorambucil (leukeran), cis-platinum ("non-classical" alkylating agent), carbo-platinum ("non-classical" alkylating agent), carmustine (BCNU), thiotepa, busulfan (myleran) 2.vinca alkaloids and related substances such as vincristine, vinblastine, VP-16; 3.anthracycline antibiotics such as doxorubicin (adriamycin), actinomycin D, daunorubicin (daunomycin), bleomycin, idarubicin, mitoxantrone 4.glucocorticoids such as prednisone/prednisolone, triamcinolone (vetalog), 5.inhibitors of protein/DNA/RNA synthesis, methotrexate, 6-thioguanine, 5-fluorouracil (5-FLU), cytosine arabinoside (ara-C, cytosar), L-asparaginase (Elspar), dacarbazine (DTIC), hydroxyurea (hydrea), procarbazine (matulane) and 6. miscellaneous agents such as paclitaxel.

Examples of therapeutic agents that may be administered with galactomannan to reduce their toxicity or enhance efficacy include the following: Anti-infectives including antibiotics, antivirals and vaccines, antineoplastics, cardiovascular drugs including antiarrythmics, antihypertensives etc., central nervous system drugs including analgesics, anorectics, anticonvulsants, anti-inflammatories and tranquilizers etc. OTICS, Opthalmics, gastrointestinal including anti-ulcer drugs, anticholinergic drugs etc. hormones, respiratory drugs including allergy medications, bronchodilators and decongestants, topical drugs and vitamins and minerals. Particular examples in the above categories are provided by way of illustration. Prilosec (AstraZeneca) described in U.S. Pat. No. 4,255,431 and Prevacid (TAP) described in U.S. Pat. No. 4,628,098; Lipitor (Pfizer) an anti-cholesterol drug described in U.S. Pat. No. 5,273,995. The antihyper-lipidemic agent, Zocor (Merck) U.S. Pat. No. 4,444,784; anti-depressants such as Prozac (Eli Lilly) described in U.S. Pat. No. 4,314,081; and Zoloft (Pfizer) described in U.S. Pat. No. 4,536,518; Paxil (SmithKline Beecham) U.S. Pat. Nos. 3,923,743 and 4,007,196; 4,721,723; antipsychotic agents such as Zyprexa (Eli Lilly) hematinic agents such as Epogen (Amgen), also known as Erythropoietin, and anti-inflammatory agents such as Celebrex (Searle). The formulations and dosages are provided in the Physicians Desk Reference.

The combination of cytotoxic therapeutic agent together with galactomannan can be administered in any of the methods known in the art such as in a liquid formulation, tablet, suppository, gel, cream, transdermal or topical patch or aerosol. The formulation may be administered to a subject by any of the routes known in the art including by oral, mucosal, inhalation, or by parenteral administration as defined above.

Use of the galactomannan containing formulation can have an immediate effect of increasing the responses of patients to the chemotherapy, for example, an effect is a decrease in the dosage of the agent required for effective chemotherapy, in the presence of the formulation. The combination of 5-FU together with galactomannan can be administered in any of the methods known in the art such as in a liquid formulation, tablet, suppository, gel, cream, transdermal or topical patch or aerosol. The formulation may be administered to a subject by any of the routes known in the art including by oral, mucosal, inhalation, or by parenteral administration as defined above.

All references cited herein are incorporated by reference. The following examples are provided by way of illustrating embodiments of the invention but are not intended to be limiting.

EXAMPLES

Example 1
Loss of Acute Toxicity of the Anti-Tumor Drug 5-FU in the Presence of Galactomannan Acute systemic toxicity of the anti-tumor drug 5-FU in the presence and absence of galactomannan was evaluated in Albino Swiss mice.

Albino Swiss mice (Harlan, Indianapolis, Ind.) were used as the experimental animals for measuring toxicity of therapeutic preparations following the ICH-Guideline on the Assessment of Systemic Exposure in Toxicity Studies, March 1995. Although this study was Non-GMP, it conformed to the guidelines set forth by the following references: The current FDA, 21 CFR, Part 58—Good Laboratory Practice for Nonclinical Laboratory Studies; AAALAC, "Guide for the Care and Use of Laboratory Animals," National Research Council, 1996. (NIH) (OPRR), "Public Health Service Policy on Humane Care and Use of Laboratory Animals," Health Research Extension Act of 1985 (Public Law 99–158 Nov. 20, 1985), Reprinted 1996; USDA, Department of Agriculture, Animal and Plant Health Inspection Service, 9 CFR Ch.1 (Jan. 1, 1995) edition, Subchapter A-Animal Welfare. ISO 10993-2, 1992. The Weight/Age range: 17.8–27.3 grams/at least 34 days old (adult) weighed to nearest 0.1 gm. The mice were healthy, not previously used in other experimental procedures minimum 5 days under the same conditions as for the actual test. Animal room temperature: 68±5° F.

The animals were observed for clinical signs immediately after injection, and daily for the duration of the study. Observations conducted included all clinical and toxicologic signs. Animals were weighed prior to injection and at the end of the observation period. Animals surviving at the end of the study were sacrificed by carbon dioxide inhalation.

There were a total of 4 groups of 5 animals each. The groups were as follows: 1) NaCl (0.9%), 2) 5-FU (17 mg/mL), 3) galactomannan (4.73 mg/mL) 4) 5-FU (17 mg/mL)+galactomannan (9.06 mg/mL). The diluent in all cases was 0.9% NaCl. The test article solutions and NaCl (negative control) were injected intravenously via the tail vein at a dose of 0.5 mL/mouse.

The galactomannan which in nature has a molecular weight of about 800,000 D was hydrolyzed to provide a galactomannan having an average molecular weight of 215,000 D. The galactomannan from this source has a galactose to mannan ratio of 2.2.

Galactomannan was isolated from *Gleditsia triacanthos*: (Honey locust, or Sweet-locust, or Thorny-locust) Fabaceae (family Leguminosae; Legume family, Bean family). Honey locust seeds, like those of many leguminous species, have impermeable coats and thus remain viable for long periods of time. Cleaned seeds average about 6,170/kg (2,800 lb), that is about 162 mg/seed (Vines, R. A. Trees, Shrubs, and Woody Vines of the Southwest University of Texas Press, Austin, pp. 1104 (1960). Viability can be retained for several years when seeds are stored in sealed containers at 0° to 7° C. (32° to 45° F.) (Bonner, F. T., Burton, J. D., and Grigsby, H. C., *Gleditsia* L. Honeylocust, In Seeds of Woody Plants in the United States, pp. 431–433. U.S. Department of Agriculture, Agriculture Handbook 450, Washington, DC, pp. 883 (1974)). The beans of some cultivars contain as much as 12 to 13% protein, and the pods contain up to 42% carbohydrates (Matoon, H. G., Farm Use for Tree Crops, Forest Leaves, 33, 5–7, 10–11 (1943); Stoutemyer, V. T., O'Rourke, F. L., and Steiner, W. W., Some Observations on the Vegetable Propagation of Honey Locust, J. Forestry, Vol. 42, pp. 32–36 (1944). Seeds were the primary source from which galactomannan was isolated.

Isolation, Purification, and Characterization of Galactomannan from *Gleditsia Triacanthos*

(a) Disruption of Seeds.

Seeds were milled, and the obtained material (crude particles) was placed into 85% ethanol in a flask equipped with a condenser, at a ratio of 10 g of milled seeds to 100 ml of ethanol. The flask was placed into a water bath and the mixture was boiled for 45 min, to eliminate low-molecular weight carbohydrates and pigments. The settled (or filtered) material was washed with a small amount of 85% ethanol and air-dried.

(b) Water Extraction.

Approximately five volumes of water were added to the air-dried material, and the mixture was left for 6 to 10 hrs to swell. Then five more volumes of water were added, the mixture was homogenized in a blender, and then stirred continuously for 9 hours at room temperature. Some more water should be added during the homogenization and/or stirring, to make the final ratio of water and the initial dried material (w/w) equal to 40.

(c) Precipitation with Ethanol.

The mixture was centrifuged at 10,000 g for 30 min; the water extract was collected, the precipitate was washed with water under stirring and centrifuged again, and the washing-centrifugation procedure was repeated. All three water extracts were combined, the resulted volume was measured and recorded.

A 10-mL volume was taken, and mixed with a 10-mL volume of 96% ethanol under stirring. Precipitation of a galactomannan is observed. The whole mixture was placed into refrigerator (4° C.) overnight, the precipitate was centrifuged, collected, and washed three times with 75% ethanol with the accompanying stirring and centrifugation. Liquid phases after each centrifugation were discarded. The final fibrous precipitate was air-dried and weighed. The yield of the galactomannan was within 20% to 26% of the weight of the initial seeds.

Since the final figure gives the yield of the galactomannan in a 10-mL volume of the extract (see above), total amount of the galactomannan in the whole volume of the extract was calculated.

The precipitation/centrifugation procedure was repeated with the whole volume of the extract (less 10-mL removed in the preceding step), except the final air-drying was not complete, and the final material should be slightly wet. That is why a separate "calibration" isolation of galactomannan was needed, namely to calculate a total amount of the polysaccharide in the whole extract for the follow-up purification.

(d) Further Purification.

The wet galactomannan was dissolved in water, aiming at 10 mg/mL concentration. In order to reach such a concentration, the galactomannan was left to swell in water at 40°–50° C., and then the mixture was agitated using a homogenizer. To the resulting solution, a fresh Fehling reagent solution (see below) was added (at the ratio of 2–3 mL per 100 mL) under continuous stirring, to precipitate a galactomannan-$Cu^{+2}$ complex. At the end of the precipitation procedure, the mother liquor should be clear and slightly green-blue colored. An excess of the Fehling reagent solution should be avoided, since it can dissolve the forming precipitate.

The resulting precipitate was allowed to stay for 4 hours at room temperature. After the first hour, it is recommended to take an aliquot of the mother liquor and add a few drops of the Fehling reagent solution, in order to verify a completion of the precipitation. After 4 hours, the mixture was centrifuged, the precipitate was washed with cold water (at about 10° C.), and centrifuged again. The mother liquor was discarded.

To recover the galactomannan from its copper complex, the precipitate was transferred into a pre-cooled in a freezer and put on ice porcelain mortar, and a cold (10° C.) 5% hydrochloric acid in 96% ethanol (v/v) was added to cover the precipitate. The precipitate was sheared with a pestle to such an extent, that the material released all the dye into the solution, and converted from gel back to a fibrous material. To facilitate the shearing process, if necessary, a little amount of solution of the acid in ethanol can be added.

Four volumes of 80% ethanol (per a volume of the precipitate) were added to the mixture in the mortar, and the resulting precipitate was isolated by centrifugation. It was washed 3 to 5 times with 80% ethanol, with a centrifugation after each washing (for a complete removal of copper salt), and air-dried for 1–2 hours.

The yield of the purified galactomannan was 13% to 18% from the weight of the initial seeds.

(e) Attenuation of the Molecular Weight.

The purified galactomannan was placed into a flask (equipped with a condenser, to be later used for boiling) and dissolved in water at concentration of 6–7 mg/mL. This can be achieved after swelling (at 45°–50° C.) and stirring of the material at this temperature. The pH of the resulting viscous solution was adjusted to 2.0–2.3, using 1N hydrochloric acid. The flask equipped with a condenser was placed onto a boiling water bath for 2½ hours.

After hydrolysis, the liquid was filtered and collected, and the precipitate discarded. The liquid, that was a solution of a partially depolymerized galactomannan (DG), was neutralized with 1N NaOH to pH of 6.0–6.5, and the DG was precipitated with 1.5 volumes of 96% ethanol under continuous stirring. The precipitate and the mother liquor were placed in a refrigerator. The next day the precipitate was centrifuged, washed with 75% ethanol, and centrifuged again. The precipitate was washed with 85% ethanol, centrifuged, washed with 96% ethanol, and centrifuged again. The resulting partially depolymerized galactomannan precipitate was dried over $P_2O_5$. Its molecular weight was determined (in a separate experiment, the procedure see below) as 215,000 D, and mannose/galactose ratio was 2.2. Yield was 11% to 14% from weight of the initial seeds.

(f) Preparation of Fehling Reagent Solution.

The reagent solution consists of two solutions, A and B, in equal volumes.

Solution A: Dissolve in water 34.6 g of $CuSO_4$, add a few drops of $H_2SO_4$, and add water to the final volume of 500 mL.

Solution B: Dissolve in water 60 g of NaOH and 173 g of $KNaC_4H_4O_6 \times x4H_2O$, and add water to the final volume of 500 mL.

Solutions A and B are combined in equal volumes immediately before using Feling reagent solution. Solutions A and B can be safely stored for two years.

(g) Complete Acid Hydrolysis (for Determination of Mannose/Galactose ratio in Galactomannans).

5 mg of galactomannans were placed into a glass tube and 0.5 mL of 2N sulfuric acid was added. The tube was then fused and placed into a boiling water bath for four hours. The resulting solution was diluted with an equal volume of water, and neutralized to pH 5.5–6.0 (pH is monitored with a litmus paper) with anion exchangers Dowex-1 or Dowex-2 in their $HCO_3^-$ form. The solution was filtered, and the liquid was evaporated (e.g., using a rotor evaporator) to dryness.

(h) Determination of Mannose/Galactose Ratio in Galactomannans.

The dried acid hydrolyzate (see above) was mixed in a small flask with 1 mL of water and 25 mg of sodium borohydride, and left for 4–5 hours at room temperature for aldehyde groups of monosaccharides to be reduced. Then 1 mL of water was added, and the mixture was neutralized to pH 5.5–6.0 adding Dowex-50 in its $H^+$-form. The pH was monitored using litmus paper. The liquid was filtered, collected, and completely dried.

The dry residue was mixed with 1–2 mL of methanol, agitated by shaking, and dried (in order to remove boric acid as its volatile methyl ether derivative). This step was repeated two to three times, until the white residue of boric acid had disappeared. The flask then were placed into a vacuum desiccator for two hours, and the resulting sugar alcohols were acetylated as follows:

0.3 mL of water-free distilled pyridine and 0.3 mL of water-free distilled acetic anhydride were added into the flask with dried sugar alcohols, the flask was tightly closed using a ground glass stopper and placed into boiling water bath for 60–75 min. After it the flask is removed from the bath, carefully opened, and the reaction is stopped by addition of 1 mL of methanol. The resulting mixture of pyridine and acetic ester is evaporated at 30°–40° C. using a rotary evaporator. In order to facilitate the evaporation, 1–2 mL of methanol and 1–2 mL of heptane (in that order) should be added 2–3 times in the flask. The obtained dry residue is mixed with 0.2–0.5 mL of chloroform, and the resulting solution is injected into a gas-liquid chromatograph. As an option, chromatography columns packed with 5% XE 60 on chromatone N-AW can be used. A ratio of mannose to galactose is equal to a ratio of a relative area of their respective peaks, which are identified using pure mannose and galactose as calibration sugars.

(i) Viscosity of Galactomannan Solutions, and Molecular Weight of Galactomannan.

Relative viscosity of water solutions of galactomannan is determined using the Ostwald or Ubbelohde type viscometers, calibrated with water efflux times at 25° C. Efflux times for a series of concentrations of galactomannan in the range of 5.0 to 0.5 mg/mL are determined. Data obtained are calculated as follows:

$$\eta_{rel} = \tau/\tau°,$$

where relative viscosity is equal to the ratio of efflux times for the galactomannan solution and water (at their equal volumes), and is determined at several galactomannan concentrations. For a series of galactomannan concentrations (C, mg/mL), specific viscosity is determined for each galactomannan concentration:

$$\eta_{sp} = \eta_{rel} - 1,$$

and a graph of $\eta_{sp}/C$ from C, as well as $\ln \eta_{sp}/C$ from C is plotted. Both straight lines are extrapolated to the zero concentration of galactomannan (C=0), giving the intrinsic viscosity [η] of the galactomannan.

Molecular weight of the galactomannan is calculated from its intrinsic viscosity as $$[\eta] = 0.168 \times DP^{0.98},$$

where DP is degree of polymerization. Since the "molecular weight" of a single repetitive unit in galactomannan is 162, molecular weight (MW) of the galactomannan is MW=162×DP.

The galactomannan was found to have increased solubility in a solution containing 5-FU. The 5-FU was formulated for intravenous injection at the concentration and pH provided for in the Physician's Desk Reference.

A single dose intravenous injection of the 5-FU alone or 5-FU together with galactomannan preparations was provided via the tail vein at a dose of 0.5 mL/mouse at the doses described below in (1)–(4) and observed for clinical signs immediately after injection, and daily for the duration of the study.

There were a total of 3 groups of 5 animals each. The groups were as follows: 1) 0.9% NaCl only, 2) 5-FU only (17 mg/mL) 3) galactomannan (4.73 mg/mL) and 5-FU (17 mg/mL)+galactomannan (9.06 mg/mL).

The dose of 5-FU was 20% above $LD_{50}$ i.e. 420 mg/kg compared with 340 mg/kg for an $LD_{50}$.

0.9% NaCl was used as a diluent. Animals were weighed prior to injection and at the end of the observation period. Animals surviving at the end of the study were sacrificed by carbon dioxide inhalation.

As the 5-FU was injected intravenously at the $LD_{50}$ dose, mortality was expected in 50% of the animals. The ability of the galactomannan to reduce the toxicity of $LD_{50}$ dose of 5-FU was measured by presence or absence of mortality in animals injected with the combination of 5-FU and galactomannan.

TABLE 1

| Group | Animal # | Body Weight (g) Day 0 Jan. 09, 2001 | Day 17 Jan. 26, 2001 | Weight Change | Signs of Toxicity # |
|---|---|---|---|---|---|
| NaCl | 1 | 19.0 | 26.2 | 7.2 | None |
|  | 2 | 22.1 | 24.8 | 2.7 | None |
|  | 3 | 21.6 | 25.4 | 3.8 | None |
|  | 4 | 18.7 | 25.3 | 6.6 | None |
|  | 5 | 17.5 | 24.9 | 7.4 | None |
| 5-FU | 6 | 20.4 | 22.1 | 1.7 | L, P |
|  | 7 | 20.6 | * | — | D |
|  | 8 | 19.4 | * | — | D |
|  | 9 | 22.5 | 24.0 | 1.5 | L, P |
|  | 10 | 21.2 | * | — | D |
| GM | 21 | 18.4 | 22.4 | 4.0 | None |
|  | 22 | 21.7 | 26.3 | 4.6 | None |
|  | 23 | 20.4 | 25.2 | 4.8 | None |
|  | 24 | 22.6 | 27.1 | 4.5 | None |
|  | 25 | 22.5 | 27.5 | 5.0 | None |
| 5-FU/GM | 41 | 19.8 | 26.8 | 7.0 | None |
|  | 42 | 20.8 | 25.9 | 5.1 | None |
|  | 43 | 20.3 | 27.1 | 6.8 | None |
|  | 44 | 18.8 | 24.9 | 6.1 | None |
|  | 45 | 22.4 | 27.5 | 5.1 | None |

Summary of clinical observations. *toxicity observed. Animals died before the end of the study.
L—lethargy, P—piloerection, D—death. All of the mice were male.

The in-life portion of this acute systemic toxicity test was originally 14 days. However, the first mortality was observed on day 13. Thus the in-life duration of the study was extended to 17 days.

Animals injected with NaCl alone, or the polysaccharides alone did not show any signs of toxicity and all the animals survived to the end of the study. All the animals gained wieght by the end of the study. Moreover, no signs of toxicity or mortality were observed in the animals injected with 5-FU and galactomannan where the animals gained weight similar to the controls. This result was in marked contrast to the results in mice treated with 5-FU.

Example 2
Loss of Acute Toxicity of the Anti-Tumor Drug Adriamycin in the Presence of Galactomannan.

Acute systemic toxicity of the anti-tumor drug adriamycin in the presence and absence of mannan was evaluated in Albino Swiss mice. Mice were bred as described Example 1. Experimental procedures followed approved governmental guidelines as described in Example 1.

The galactomannan was derived from *Medicago falcata*. The isolated galactomannan was cleaved to obtain a preparation with an average molecular weight of 83,000 D. The ratio of galactose to mannose for this preparation was 1.13. Galactomannan was isolated from *Medicago falcata* as follows:
Isolation, Purification, and Characterization of Biologically Active Galactomannan from *Medicago falcata* (Lucerne).

Seeds were the primary source of the galactomannan that was isolated from *Medicago falcata* in this study.
(a) Disruption of Seeds (as in Example 1)
(b) Benzene Treatment The dried material was mixed with 3× volume of distilled benzene, and the mixture was periodically stirred for about 45 min. The material was filtered, washed with a small amount of distilled benzene, and air-dried.

(c) Water Extraction (as in Example 1)
(d) Precipitation with Ethanol

The mixture was centrifuged at 10,000 g for 30 min, the water extract was collected, the precipitate was washed with water under stirring and centrifuged again, and the washing-centrifugation procedure was repeated. All three water extracts were combined, and concentrated four-fold at 60°–65° C. using a rotor evaporator. The resulted volume was centrifuged at 5,000 rpm for 60 min for removal of proteins, which were coagulated at the bottoms of centrifuge vessels. The resulted volume was measured and recorded.

A 5 mL-volume was taken, and mixed with a 5 mL-volume of 96% ethanol under stirring. Precipitation of a galactomannan was observed. The whole mixture was placed into refrigerator (4° C.) overnight, the precipitate was centrifuged, collected, and washed three times with 75% ethanol with the accompanying stirring and centrifugation. Liquid phases after each centrifugation were discarded. The final fibrous precipitate was air-dried and weighed. The yield of the galactomannan should be within 6% to 8% of the weight of the initial seeds.

Since the final figure gives the yield of the galactomannan in a 5 mL-volume of the extract (see above), total amount of the galactomannan in the whole volume of the extract was calculated.

The precipitation/centrifugation procedure was repeated with the whole volume of the extract (less 5 mL removed in the preceding step), except the final air-drying was not complete, and the final material should be slightly wet. That is why a separate "calibration" isolation of galactomannan was needed, namely to calculate a total amount of the polysaccharide in the whole extract for the follow-up purification.
(e) Further Purification (see Example 1)

The yield of the purified galactomannan should be 6.5% from the weight of the initial seeds.
(f) Preparation of Fehling Reagent Solution as in Example 1.
(g) Preparation of Dowex resins.

Dry resins are left in water overnight for swelling, then a swollen resin is placed on glass filter and the respective water solutions are passed through. For Dowex-1 to be charged to its anionic form, 4% sodium bicarbonate solution is slowly passed through, and then the resin is washed with water until passing through water has the neutral pH (monitored with litmus paper). For Dowex-50 to be charged to its cationic ($H^+$) form, 3–4 volumes of 1N hydrochloric acid is passed through, and then the resin is washed with water as described above until pH of water is neutral.
(h) Complete Acid Hydrolysis (as in Example 1).
(i) Determination of Mannose/Galactose Ratio in Galactomannans (see Example 1)
(j) Viscosity of Galactomannan Solutions, and Molecular Weight of Galactomannan (see Example 1).

The galactomannan was found to have increased solubility in a solution containing adriamycin A. The adriamycin was formulated for intravenous injection at the concentration and pH provided for in the Physician's Desk Reference.

A single dose intravenous injection of the adriamycin alone or adriamycin together with galactomannan preparations was provided via the tail vein at a dose of 0.5 mL/mouse at the doses described below in (1)–(3) and observed for clinical signs immediately after injection, and daily for the duration of the study.

There were a total of 3 groups of 5 animals each. The groups were as follows: 1) 0.9% NaCl only, 2) Adriamycin only (1.1 mg/mL) and Adriamycin (1.1 mg/mL)+ galactomannan (7.2mg/mL). $LD_{50}$ for Adriamycin (i.v. in mice) is 21.1 mg/kg (The Merck Index, $12^{th}$ Edition, p 582).

0.9% NaCl was used as a diluent. Animals were weighed prior to injection and at the end of the observation period. Animals surviving at the end of the study were sacrificed by carbon dioxide inhalation.

As the Adriamycin was injected intravenously at the $LD_{50}$ dose, mortality was expected in 50% of the animals. The ability of galactomannan to reduce the toxicity of $LD_{50}$ dosed of Adriamycin was measured by presence or absence of mortality in animals injected with the combination of Adriamycin and the particular polysaccharide.

Results

Animals injected with NaCl alone did not show any signs of toxicity and all the animals survived to the end of the study. All the animals gained weight by the end of the study.

Three out of 5 animals in the Adriamycin alone group (one animal each on day 1, day 4 and day 5) died before the end of the study. The surviving 2 animals lost weight by the end of the study (Table I).

One out of 5 animals injected with Adriamycin and galactomannan (one animal on day 4) died before the end of the study. Three out of four remaining animals lost weight by the end of the study. The fourth animal gained very little weight (Table I). Observations conducted included all clinical and toxicologic signs. Adriamycin only at the $LD_{50}$ dose death in 3 out of 5 mice. However, mice injected with the combination of galactomannan and a $LD_{50}$ dose of Adriamycin resulted in the death of only one mouse demonstrating that galactomannan has the ability to decrease the toxicity of the anti-tumor Adriamycin.

TABLE 2

Effect of Galactomannan (GM) when co-administered with Adriamycin

| Group | Animal # | Day 0 Feb. 05, 2001 | Day 14 Feb. 19, 2001 | Weight Change | Signs of Toxicity # |
|---|---|---|---|---|---|
| NaCl | 1 | 21.8 | 26.0 | 4.2 | None |
|  | 2 | 17.8 | 30.2 | 12.4 | None |
|  | 3 | 27.0 | 29.9 | 2.9 | None |
|  | 4 | 23.6 | 27.5 | 3.9 | None |
|  | 5 | 25.7 | 33.2 | 7.5 | None |
| Adriamycin | 6 | 27.3 | 25.2 | −2.1 | None |
|  | 7 | 22.7 | 19.1 | −3.6 | None |
|  | 8 | 21.0 | * | — | D |
|  | 9 | 25.2 | * | — | D |
|  | 10 | 21.6 | * | — | D |
| Adriamycin/GM | 16 | 25.3 | * | — | D |
|  | 17 | 25.1 | 23.2 | −1.9 | None |
|  | 18 | 25.8 | 24.2 | −1.6 | None |
|  | 19 | 24.7 | 23.7 | −1.0 | None |
|  | 20 | 24.5 | 25.6 | 1.1 | None |

Summary of clinical observations. *toxicity observed. Animals died before the end of the study.
D = death. Male animals were used throughout the study Example 3

Synergistic Effect on Tumor Reduction of the Anti-Tumor Drug 5-FU in the Presence of Galactomannan from *Gleditsia triacanthos*.

Response of subcutaneously implanted COLO 205 human colon tumor to treatment with a cytotoxic chemotherapeutic agent, 5-fluorouracil (5-FU), in the presence and absence of galactomannan was evaluated in male NCr-nu athymic nude mice.

Male NCr-nu athymic nude mice (Frederick Cancer Research and Development Center, Frederick, Md.) were acclimated in the laboratory one week prior to experimentation. The animals were housed in microisolator cages, five per cage in a 12-hour light/dark cycle. The animals received filtered water and sterile rodent food ad libitum. The animals were observed daily and clinical signs were noted. Weight of the animals was in the range of 25–34 g at 13th day of the study, that is the first day of treatment initiation. The mice were healthy, not previously used in other experimental procedures.

Thirty to forty mg fragments of COLO 205 human colon tumor were implanted subcutaneously (s.c.) in mice near the right axillary area using a 12-gauge trocar needle and allowed to grow. Tumors were allowed to reach 75–198 mg in weight (75–198 mm$^3$ in size) before the start of treatment. A sufficient number of mice were implanted so that tumors in a weight range as narrow as possible were selected for the trial on the day of treatment initiation (day 13 after tumor implantation). Those animals selected with tumors in the proper size range were divided into the various treatment groups. The median tumor weights in each treatment group ranged from 94 to 117 mg.

Study duration was seventy days after tumor implantation, or fifty-six days after treatment initiation. Any animal whose tumor ulcerated or reached 4000 mg in size was sacrificed prior to study termination.

The individual animal's time to reach the evaluation size (time to reach two tumor mass doubling) was used in the calculations of the overall delay in the growth of the median tumor [(T−C)/C×100, %] and as the endpoint in life tables analysis (stratified Kaplan-Meier estimation followed by the Mantel-Haenszel log-rank test) in order to statistically compare the growth data between groups.

The s.c. tumors were measured and the animals were weighed twice weekly starting with the first day of treatment. Tumor volume was determined by caliper measurements (mm) and using the formula for an ellipsoid sphere: L×W2/2=mm$^3$, where L and W refer to the larger and smaller dimensions collected at each measurement. This formula was also used to calculate tumor weight, assuming unit density (1 mm$^3$=1 mg).

The galactomannan which in nature has a molecular weight of about 800,000 D was cleaved to provide a galactomannan having an average molecular weight of 215,000 D. The galactomannan from this source has a galactose to mannan ratio of 2.2. Source of galactomannan and its isolation, purification and characterization are as described in Example 1

Galactomannan was administered intravenously (i.v.) once every four days for a total of three injections (q4d×3) at a dosage of 120 mg/kg/dose (except of a 60 mg/kg dosage, see below) or was co-administered as one injection with 5-FU on the same q4d×3 treatment schedule at dosages of 120 mg/kg/dose of galactomannan and 75 mg/kg/dose of 5-FU. 5-FU alone was administered i.v. on the same q4d×3 treatment schedule at dosages of 75 mg/kg/dose. 5-FU was formulated in saline fresh on each day of treatment at a concentration of 3.75 mg/mL, at pH 8.4–9.0 (with 1N NaOH). In the groups where galactomannan and 5-FU were co-administered, galactomannan powder was dissolved in the 5-FU solution to yield the galactomannan concentration of 6 mg/mL and 5-FU concentration of 3.75 mg/mL. Both individual compounds and their mixture were administered by exact body weight with injection volume being 0.2 mL/10 g body weight.

There were a total of seven groups of 10 animals each, s.c.-implanted with COLO 205 human colon tumor xenografts. The groups were treated on day 13 after tumor implantation on q4d×3 schedule (except for the last group, that was treated for comparative purposes with a lower dose of galactomannan alone on q1d×5 schedule, see Table 1) as follows:

(1) Saline (NaCl, 0.9%),
(2) 5-FU (75 mg/kg),
(3) Galactomannan (120 mg/kg),
(4) 5-FU (75 mg/kg)+Galactomannan (120 mg/kg),
(5) 5-FU (375 mg/kg),
(6) 5-FU (375 mg/kg)+Galactomannan (120 mg/kg),
(7) Galactomannan (60 mg/kg) for five consecutive days (q1d×5).

The data (except of groups 5 and 6, see below) are shown in Table 1.

TABLE 1

| | Animal response in the following five groups (10 mice in each at treatment initiation) | | | | |
|---|---|---|---|---|---|
| | Saline (control) q4d × 3 | 5-FU (75 mg/kg) q4d × 3 | Galactomannan (GM) (120 mg/kg) q4d × 3 | 5-FU (75 mg/kg) + GM (120 mg/kg) q4d × 3 | GM (60 mg/kg) q1d × 5 |
| Median days to 2× doubling of tumor weight | 12.5 | 23.7 | 15.5 | 56.0 | 20.0 |
| Animals with small tumors (20% and less) compared to median of untreated after 4–8 weeks of treatment | 0 | 1 | 1 | 4 | 0 |
| Tumor complete regression after 56 days of treatment | 0 | 0 | 0 | 1 | 0 |
| Median tumor weight (on days after treatment initiation) | | | | | |
| Day 0 | 111 mg | 101 mg | 100 mg | 111 mg | 117 mg |
| Day 3 | 189 mg | 135 mg | 162 mg | 144 mg | 162 mg |
| 1 week | 415 mg | 198 mg | 258 mg | 209 mg | 216 mg |
| 2 weeks | 527 mg | 245 mg | 320 mg | 158 mg | 319 mg |
| 3 weeks | 968 mg | 352 mg | 629 mg | 126 mg | 512 mg |
| 4 weeks | 1296 mg | 527 mg | 959 mg | 144 mg | 690 mg |
| 5 weeks | 2450 mg | 990 mg | 1692 mg | 288 mg | 1116 mg |
| 6 weeks | 1651 mg | 1345 mg | 1690 mg | 288 mg | 1421 mg |
| 7 weeks | 2432 mg | 1881 mg | 1764 mg | 320 mg | 1152 mg |
| 8 weeks | 2058 mg | 2254 mg | 1813 mg | 405 mg | 1152 mg |
| Animals died (on weeks after treatment initiation) | | | | | |
| 1 week | 0 | 1 (nonspecific) | 0 | 0 | 1 (nonspecific) |
| 2 weeks | 0 | 2 (nonspecific) | 0 | 4 (nonspecific) | 0 |
| 3 weeks | 1 | 0 | 0 | 0 | 0 |
| 4 weeks | 0 | 0 | 0 | 1 | 1 |
| 5 weeks | 0 | 1 | 0 | 0 | 0 |
| 6 weeks | 1 (sac) | 0 | 1 (sac) | 0 | 0 |
| 7 weeks | 1 (sac) | 0 | 0 | 1 (sac) | 1 (sac) |
| 8 weeks | 2 (sac) | 1 (sac) | 1 (sac) | 0 | 0 |
| Total | 5 | 5 | 2 | 6 | 3 |
| Mean survival time, days | 14.2 | 23.7 | 19.2 | 44.2 | 18.1 |

(sac)—sacrificed animals

Control untreated tumors grew well in all mice, with a median to quadrupling of tumor weight equals to 12.5 days. There was no tumor regression after 56 days of the study, and there was practically no tumor reduction. Median tumor weight increased from 111 mg at treatment initiation (in this case with saline only) to 2000–2450 mg after 5–8 weeks. One mouse died and four more animals were sacrificed to the end of the study due to either a large tumor (>4 grams) or tumor ulceration. Mean survival time calculated using parametric models and stratified Kaplan-Meier estimation followed by the Mantel-Haenszel log-rank test was equal to 14.2 days.

5-FU administered alone at a dosage of 375 mg/kg/dose at q4dx3 schedule was lethal, causing nine death out of ten mice within 10 days after the treatment initiation (a single LD50 dose for 5-FU in mice was reported to be 340 mg/kg, see the Physician's Desk Reference 48th Edition (1994), pp. 1925). The same treatment in a combination with galactomannan (120 mg/kg/dose) caused seven deaths within the same time period. The data are not shown in Table 1.

A dosage of 75 mg/kg/dose of 5-FU (that is, 225 mg/kg total dose over 8 days) was in excess of the maximum tolerated dosage producing three treatment-related deaths out of ten mice within two weeks. The treatment caused a delay in a median to quadrupling of tumor weight from 12.5 to 23.7 days. Again, there was no tumor regression after 56 days of the study, however, two relatively small tumors were observed that grew from 75 mg each at initiation of treatment to 126 mg and 567 mg by the end of the study. Median tumor weight increased from 101 mg at treatment initiation to 2254 mg after 56 days of the study. Three nonspecific deaths were observed within two weeks (apparently, due to toxicity), one mouse died on fifth week, and one more was sacrificed to the end of the study because of tumor ulceration. Mean survival time shifted from 14.2 days (control, untreated animals) to 23.7 days.

Galactomannan at a dosage of 120 mg/kg/dose administered alone on a q4dx3 schedule was well tolerated without deaths or body weight loss, with a median to quadrupling of tumor weight equals to 15.5 days, that is slightly (3 days) delayed compared with untreated animals. There was no tumor regression after 56 days of the study, however, two relatively small tumors (compared to median tumor weight) were observed that grew from 100 mg and 126 mg at initiation of treatment to 270 mg and 729 mg, respectively, by the end of the study. Median tumor weight increased from 100 mg at treatment initiation to 1813 mg after 56 days of the study, that is noticeably less compared to 2000–2450 mg for untreated animals, and 2254 mg for 5-FU (75 mg/kg/dose)-treated animals. Two mice were sacrificed to the end of the study, one due to a large tumor (>4 grams), another because of tumor ulceration. Mean survival time shifted from 14.2 days (control, untreated animals) to 19.2 days.

A change of the administration schedule for galactomannan from 120 mg/kg/dose, once in four days, three injections (q4dx3) to 60 mg/kg/dose every day, five injections (q1dx5) caused a further delay in quadrupling of the tumor weight, from 12.5 days in control (untreated animals) to 15.5 days and 20.0 days, respectively (see Table 1). Mean survival time was close for the two schedules for galactomannan administration, namely 19.2 and 18.1 days (Table 1), however, median tumor size was significantly smaller with a more frequent administration of a lower dose of galactomannan (1813 mg and 1152 mg, respectively), and even smaller compared with that for 5-FU administration (2254 mg).

Co-administration of galactomannan (120 mg/kg/dose) and 5-FU (75 mg/kg/dose) on a q4dx3 schedule brought a remarkable effect. It caused a significant delay in quadrupling of tumor weight, from 12.5 days for untreated animals (control) and 23.7 and 15.5 days for 5-FU alone and galactomannan alone, respectively, to 56.0 days for their combination. There was one tumor that completely disappeared by the end of the study; it went from the initial 75 mg to 126 mg on a third day after treatment initiation (that is, after the first injection) and further to 144 mg after the second and third injections, and after two weeks on the study it decreased to barely detectable one, and then completely disappeared. Two more tumors were of a relatively small size (352 and 405 mg) by the end of the study. Overall, median tumor weight increased from 111 mg at treatment initiation to only 405 mg after 56 days of the study, that is significantly less compared to 2000–2450 mg for untreated animals, and 2254 mg for 5-FU (75 mg/kg/dose)-treated animals. Toxicity, however, was still there, with four nonspecific deaths within two weeks, one death after four weeks, and one sacrificed mouse to the end of the study because of tumor ulceration. Mean survival time shifted from 14.2 days (control, untreated animals) and 23.7 days (5-FU treatment) to 44.2 days for a combination treatment.

Thus, this result was in marked contrast to the results in cancer-carrying mice treated with 5-FU alone.

What is claimed is:

1. A method for treating a cancer in a subject, comprising:
   obtaining a mixture of galactomannan polysaccharide and an effective dose of a chemotherapeutic agent in a pharmaceutically acceptable formulation; and
   administering the formulation to the subject so as to treat the cancer.

2. A method according to claim 1, wherein the mixture contains an amount of galactomannan and the chemotherapeutic agent in a ratio suitable for reducing a toxic effect in the subject, the toxic effect associated with administration of the chemotherapeutic agent absent galactomannan.

3. A method according to claim 1, wherein the mixture contains an amount of galactomannan and the chemotherapeutic agent in a ratio suitable for enhancing efficacy of chemotherapeutic effect for treating the cancer.

4. A method according to claim 1, wherein the size of the galactomannan is in the range of 20,000 to 600,000 D.

5. A method according to claim 4, wherein the galactomannan has a molecular weight in the range of 90,000 to 415,000 D.

6. A method according to claim 4, wherein the galactomannan has a molecular weight in the range of 40,000–200,000 D.

7. A method according to claim 4, wherein the galactomannan has an average molecular weight of 48,000 D.

8. A method according to claim 4, wherein the galactomannan has an average molecular weight of 83,000 D.

9. A method according to claim 4, wherein the galactomannan has an average molecular weight of 215,000 D.

10. A method according to claim 1, wherein the galactomannan is β 1,4 D-galactomannan.

11. A method according to claim 4, wherein galactomannan includes a ratio of mannose to galactose in the range of 1.0–3.0.

12. A method according to claim 11, wherein galactomannan includes a ratio of 2.6 mannose to 1.5 galactose.

13. A method according to claim 11, wherein galactomannan includes a ratio of 2.2 mannose to 0.9 galactose.

14. A method according to claim 11, wherein the galactomannan includes a ratio of 1.13 mannose to 1 galatose.

15. A method according to claim 11, wherein the galactomannan includes a ratio of 2.2 mannose to 1 galactose.

16. A method according to claim 1, wherein the galactomannan and the chemotherapeutic agent are present in the mixture in a ratio of 0.1:1 w/w to 10:1 w/w.

17. A method according to claim 2, wherein the mixture has a reduced toxicity of greater than 50% compared with the same dose of the agent absent galactomannan.

18. A method according to claim 2, wherein the mixture has a reduced toxicity of greater than 80% compared with the same dose of the agent absent galactomannan.

19. A method according to claim 3, wherein the mixture has an enhanced efficacy of greater than 50% compared with the same dose of the agent absent galactomannan.

20. A method according to claim 3, wherein the mixture has an enhanced efficacy of greater than 80% compared with the same dose of the agent absent galactomannan.

21. A method according to claim 1, wherein the chemotherapeutic agent is adriamycin.

22. A method according to claim 1, wherein the chemotherapeutic agent is 5-FU.

23. A method according to claim 1, wherein the cancer is any of chronic leukemia, breast cancer, sarcoma, ovarian carcinoma, rectal cancer, throat cancer, melanoma, colon cancer, bladder cancer, lung cancer, mammary adenocarcinoma, gastrointestinal cancer, stomach cancer, prostate cancer, pancreatic cancer, or Kaposi's sarcoma.

24. The method according to claim 1, wherein the cancer is any of breast cancer, colon cancer, or pancreatic cancer.

25. The method according to claim 23, wherein the subject is a human subject.

* * * * *